US011871789B2

(12) United States Patent
Mironov et al.

(10) Patent No.: US 11,871,789 B2
(45) Date of Patent: *Jan. 16, 2024

(54) AEROSOL-GENERATING DEVICE WITH DETACHABLY INSERTABLE HEATING COMPARTMENT

(71) Applicant: Philip Morris Products S.A., Neuchatel (CH)

(72) Inventors: Oleg Mironov, Cudrefin (CH); Oleg Fursa, Gempenach (CH); Jerome Christian Courbat, Cortaillod (CH); Tony Reevell, London (GB); Andreas Michael Rossoll, Le Mont-sur-Lausanne (CH); Enrico Stura, Palezieux-Village (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/899,238

(22) Filed: Aug. 30, 2022

(65) Prior Publication Data

US 2022/0408827 A1 Dec. 29, 2022

Related U.S. Application Data

(63) Continuation of application No. 16/637,032, filed as application No. PCT/EP2018/071261 on Aug. 6, 2018, now Pat. No. 11,478,018.

(30) Foreign Application Priority Data

Aug. 9, 2017 (EP) ..................................... 17185550

(51) Int. Cl.
*A24F 13/00* (2006.01)
*A24F 40/465* (2020.01)
(Continued)

(52) U.S. Cl.
CPC .......... *A24F 40/465* (2020.01); *A24F 40/485* (2020.01); *H05B 6/108* (2013.01); *A24F 40/20* (2020.01)

(58) Field of Classification Search
CPC ....................................................... A24F 47/00
(Continued)

(56) References Cited

U.S. PATENT DOCUMENTS 10,299,514 B2 * 5/2019 Bilat ....................... A24F 40/53
11,337,464 B2 5/2022 Lee
(Continued)

FOREIGN PATENT DOCUMENTS

CN 105307526 A 2/2016
CN 206341938 U 7/2017
(Continued)

OTHER PUBLICATIONS

Office Action dated Jul. 21, 2022, in corresponding Brazilian Patent Application No. BR112020002427-9 citing documents 1 and 15 therein, 4 pages.
(Continued)

*Primary Examiner* — Phuong K Dinh
(74) *Attorney, Agent, or Firm* — Oblon, McClelland, Maier & Neustadt, L.L.P.

(57) ABSTRACT

An aerosol-generating device is provided, including: a housing having a chamber, an induction coil around at least part of the chamber; a heating compartment to receive an aerosol-generating article, being detachably insertable into the chamber, and including a cavity to receive the article; and a heating element arrangeable within and extending into the cavity in a longitudinal direction, configured to penetrate an aerosol-forming substrate included in the article and received in the cavity, the compartment further including a first open end to receive the article, and a second, base end
(Continued)

opposite the first open end, the first open end and the base end connected by side surfaces including openings and locking elements, and the chamber including recesses corresponding to the locking elements to facilitate a snap-fit when the compartment is inserted into the chamber, the compartment further including a press button to allow release of the snap-fit connection.

15 Claims, 5 Drawing Sheets

(51) Int. Cl.
  *H05B 6/10* (2006.01)
  *A24F 40/485* (2020.01)
  *A24F 40/20* (2020.01)

(58) Field of Classification Search
  USPC .................................................. 131/328–329
  See application file for complete search history.

(56) References Cited

U.S. PATENT DOCUMENTS

| | | | |
|---|---|---|---|
| 11,478,018 B2* | 10/2022 | Mironov | A24F 40/485 |
| 2015/0223292 A1 | 8/2015 | Duffield et al. | |
| 2016/0295916 A1 | 10/2016 | Malgat et al. | |
| 2016/0324215 A1 | 11/2016 | Mironov et al. | |
| 2017/0055580 A1 | 3/2017 | Blandino et al. | |
| 2017/0095002 A1 | 4/2017 | Silvestrini | |
| 2017/0119048 A1 | 5/2017 | Kaufman et al. | |
| 2017/0156403 A1 | 6/2017 | Gill et al. | |
| 2018/0027883 A1 | 2/2018 | Zuber | |
| 2018/0029782 A1* | 2/2018 | Zuber | H05B 1/0227 |
| 2018/0049472 A1 | 2/2018 | Mahler et al. | |
| 2018/0206295 A1 | 7/2018 | Duffield et al. | |
| 2021/0153555 A1 | 5/2021 | Gill | |

FOREIGN PATENT DOCUMENTS

| | | |
|---|---|---|
| GB | 2504732 A | 2/2014 |
| GB | 2527597 A | 12/2015 |
| RU | 2 613 785 C2 | 3/2017 |
| RU | 2 625 932 C2 | 7/2017 |
| WO | 2011/063970 A1 | 6/2011 |
| WO | WO 2013/127538 A1 | 9/2013 |
| WO | 2016/124550 A1 | 8/2016 |
| WO | 2017/029269 A1 | 2/2017 |
| WO | 2017/068009 A1 | 4/2017 |
| WO | 2017/068096 A1 | 4/2017 |
| WO | 2017/072148 A1 | 5/2017 |
| WO | WO 2017/075759 A1 | 5/2017 |

OTHER PUBLICATIONS

International Search Report and Written Opinion dated Nov. 12, 2018 in PCT/EP2018/071261 filed Aug. 6, 2018.

Decision to Grant dated Jun. 16, 2020, in Russian Application No. 2020105775/03(008847) (submitting English language translation only), citing documents 6 and 18-20 therein, 7 pages.

Office Action dated Jan. 28, 2021 in corresponding Japanese Patent Application No. (English Translation only), citing documents 7, 21 and 22 therein, 2 pages.

Combined Chinese Office Action and Search Report dated Jan. 17, 2022 in Chinese Patent Application No. 201880050919.8 (submitting English translation only), 10 pages.

Chinese Office Action dated Jul. 11, 2022 in corresponding Chinese Patent Application No. 201880050919.8 (with English translation), citing documents 1 and 15 therein, 21 pages.

U.S. Appl. No. 16/637,032, filed Feb. 6, 2020, 2020/0236999 A1, Oleg Mironov, et al.

* cited by examiner

AEROSOL-GENERATING DEVICE WITH DETACHABLY INSERTABLE HEATING COMPARTMENT

CROSS-REFERENCE TO RELATED APPLICATIONS

This is a continuation application of and claims benefit under 35 U.S.C. § 120 to U.S. application Ser. No. 16/637,032, filed Feb. 6, 2020, which is a U.S. national stage application of PCT/EP/2018/071261, filed on Aug. 6, 2018, which is based upon and claims the benefit of priority under 35 U.S.C. § 119 to European patent application no. 17185550.5, filed Aug. 9, 2017, the entire contents of each of which are incorporated herein by reference.

TECHNICAL FIELD

The present invention relates to an aerosol-generating device comprising a housing and an induction coil.

It is known to employ different types of heaters in aerosol-generating articles for generating an aerosol. Typically, resistance heaters are employed for heating an aerosol-forming substrate such as an e-liquid. It is also known to provide "heat not burn" devices utilizing resistance heaters, which generate an inhalable aerosol by heating but not burning an aerosol-forming substrate containing tobacco.

DESCRIPTION OF THE RELATED ART

Induction heaters offer advantages and have been proposed in the above devices. Induction heaters are for example described in US 2017/055580 A1. In induction heaters, an induction coil is arranged around a component made from a conductive material. The component may be denoted as a heating element or susceptor. A high-frequency AC current is passed through the induction coil. As a result, an alternating magnetic field is created within the induction coil. The alternating magnetic field penetrates the heating element thereby creating eddy currents within the heating element and/or hysteresis losses. These currents and/or hysteresis losses lead to a heating of the heating element. In addition to heat generated by eddy currents, the alternating magnetic field may also cause the susceptor to heat due to the hysteresis mechanism. Some susceptors may even be of a nature that no, or almost no, eddy currents will take place. In such susceptors substantially all the heat generation is due to hysteresis mechanisms. Most common susceptors are of such a kind, where heat is generated by both mechanisms. A more elaborate description of the processes and responsible for generating heat in a susceptor, when penetrated by an alternating magnetic field may be found in WO2015/177255. Inductive heaters facilitate rapid heating which is beneficial for generating an aerosol during the operation of the aerosol-generating device.

It would be desirable to have an aerosol-generating device with an induction heater in which the heating element can be easily accessed and the use of a consumable is simplified.

SUMMARY

According to a first aspect of the invention there is provided an aerosol-generating device comprising a housing having a chamber. An induction coil is disposed around at least a portion of the chamber. The device comprises a heating compartment for receiving an aerosol-generating article. The heating compartment is detachably insertable into the chamber of the housing. The heating compartment comprises a cavity configured to receive at least a portion of the aerosol-generating article. The device further comprises a heating element which is arrangeable within the cavity of the heating compartment. Preferably, the heating element extends into the cavity in a longitudinal direction of the cavity. The heating element is preferably configured to penetrate an aerosol-forming substrate comprised in the aerosol-generating article and received in the cavity.

BRIEF DESCRIPTION OF THE DRAWINGS

The invention will be further described, by way of example only, with reference to the accompanying drawings in which.

DETAILED DESCRIPTION

By providing a heating compartment which can be removed from the aerosol-generating device, the handling of a consumable may be simplified. If the consumable is inserted into the cavity of the heating compartment, the removal of the consumable may be facilitated by removing the heating compartment with the consumable still being arranged in the heating compartment. After the removal of the heating compartment, the consumable may be removed from the cavity of the heating compartment. Also, the insertion of a consumable into the aerosol-generating device may be simplified. In this regard, the consumable may be introduced into the cavity of the heating compartment before the heating compartment is inserted into the chamber of the device. After the consumable has been inserted into the heating compartment, the heating compartment together with the consumable may be inserted into the chamber of the aerosol-generating device.

The removable heating compartment may enable that the heating element within the heating compartment may be removed from the housing of the aerosol-generating device. After the removal of the heating compartment, the heating element may be easily cleaned and reintroduced into the device. Also, a new heating element may be arranged in a new heating compartment and may be introduced into the chamber of the housing.

Aerosol-forming substrate containing tobacco may be provided in the form of an aerosol-generating article. The aerosol-generating article may be provided as a consumable such as a tobacco stick. In the following, the aerosol-generating article will be denoted as a consumable. These consumables may have an elongate rod-like shape. Such a consumable is typically pushed into the cavity of the heating compartment. In the cavity, the heating element of the induction heater penetrates the aerosol-forming substrate in the consumable during insertion of the consumable. After use, the consumable is removed and replaced by a new consumable. Upon removing the consumable, residues of aerosol-forming substrate may stick to the heating element and impair the functionality of the heating element. Such residues may affect subsequent aerosol generation and are thus unwanted. By providing an accessible heating compartment, removal of the residues may be facilitated.

The heating element and coil may have an elongate shape. The heating element may have the same length as the coil. The heating element may have the shape of a pin or blade. The heating element may be solid while the coil may have a helical shape such that the heating element can be arranged within the coil. The coil may be provided as a helical wound coil with the shape of a helical spring. The coil may comprise contact elements such that an AC current can flow through the coil from a power supply. The AC current is preferably configured to operate at high frequency. For the purpose of this application, the term "high frequency" is to be understood to denote a frequency ranging from about 1 Megahertz (MHz) to about 30 Megahertz (MHz) (including the range of 1 MHz to 30 MHz), in particular from about 1 Megahertz (MHz) to about 10 MHz (including the range of 1 MHz to 10 MHz), and even more particularly from about 5 Megahertz (MHz) to about 7 Megahertz (MHz) (including the range of 5 MHz to 7 MHz).

No direct or electrical connection needs to be established between the coil and the heating element, since the magnetic field generated by the coil penetrates the heating element and thereby creates the eddy currents and/or power losses associated with the mechanism of hysteresis. The eddy currents and/or hysteresis losses are converted into heat energy. The coil as well as the heating element may be made from a conductive material such as metal. The heating element and the coil may have a circular, elliptical or polygonal shaped cross-section. The induction coil may be arranged within the housing of the device to be protected. The housing may be made from a material that does not act as a susceptor, when subjected to an alternating magnetic field. In an embodiment the housing is made from a non-conductive material such that no eddy currents are generated in the housing, and which is also not heatable through hysteresis mechanisms. In other words, the housing may be made from a non-susceptor material, for example a non-conductive, non-susceptor material. The whole housing of the device may be made from a non-conductive material. Alternatively, the section of the housing adjacent to the induction coil may be made from a non-conductive material.

The heating element may extend into the cavity in a longitudinal direction of the cavity, configured to penetrate an aerosol-forming substrate comprised in the aerosol-generating article and received in the cavity. When referring to the cavity, the term 'longitudinal' refers to the direction in which the aerosol-generating article is inserted into the cavity and the term 'transverse' refers to a direction perpendicular to the direction in which the aerosol-generating article is inserted into the cavity.

The heating element may be an integral part of the heating compartment. Alternatively, the heating element may be removably attached to the heating compartment. According to the latter aspect, the heating element can be easily cleaned or replaced.

The heating compartment may be configured to be held in the chamber of the housing by a press fit. The outer diameter of the heating compartment may essentially correspond to the inner diameter of the chamber to facilitate a press fit.

At least one air inlet may be provided at the side of the housing such that air may be drawn through the air inlet and guided past the heating element.

Except for the heating element, the heating compartment may be made of a thermally insulating material. The heating element may be made of an electrically conductive material. After operation of the induction heater, the heating compartment may be removed by a user without being too hot.

The heating compartment may comprise a first open end for inserting at least a portion of a consumable containing aerosol-forming substrate. The heating compartment may further comprise a second, base end disposed opposite the first open end. The second base end may comprise a support element for mounting the heating element. The heating compartment is configured to allow air to be drawn through the heating compartment.

The base end or the support element may limit the movement of a consumable within the cavity of the heating compartment. The base end or the support element may be arranged such that the consumable may be inserted a predefined length into the heating compartment until abutting the support element. The support element may comprise connecting elements, preferably arranged in a cross shape, for connecting the heating compartment with the heating element. Air may be drawn through apertures in the base end or the support element and through an inserted consumable adjacent to the heating element such that an aerosol can be generated by heating the heating element.

The first open end of the heating compartment may comprise a protruding rim with a width larger than the internal width of the chamber. The protruding rim section may allow the heating compartment to be gripped and removed from the chamber of the housing. The protruding rim section may prevent the heating compartment to be inserted too deep into the chamber.

The protruding rim section may be configured such that the protruding rim section has a larger outer diameter than the inner diameter of the chamber. Thus, the protruding rim section may limit the insertion of the heating compartment into the chamber. The protruding rim section may have the same outer diameter as the housing of the aerosol-generating device for facilitating a smooth outer surface when the heating compartment is inserted into the chamber. Thus, the handling of the device after the insertion of the heating compartment into the chamber of the device may be optimized.

The heating compartment may have a shape which resembles the outer shape of the consumable. The consumable may be held firmly within the cavity of the heating compartment.

The heating compartment may be movably coupled to the chamber between a first position and a second position, the first position being an operating position defined by the heating element being in contact with the aerosol-forming substrate, and the second position being an extraction position defined by the aerosol-forming substrate being partly separated from the heating element. In the second position, the heating compartment may be partly removed from the chamber of the aerosol-generating device. In this aspect, the second position may facilitate ease of removal of the aerosol-generating-article. The second position may be a position in which the aerosol-generating article is partly extracted from the chamber. The extraction from the chamber may be facilitated by a corresponding extraction of the heating compartment. After operation of the aerosol-generating device, a user may partly remove the heating compartment from the chamber. The used aerosol-generating article may still be held within the heating compartment. Due to the partial removal of the heating compartment, the heating element may then no longer fully penetrate into the aerosol-forming substrate of the aerosol-generating article. This may facilitate removal of the used aerosol-generating article requiring less force. Less force may be required, since the friction between the penetrated aerosol-forming substrate and the heating element may be reduced. Less residues of aerosol-forming substrate may be loosened by partly extracting the heating compartment from the chamber of the aerosol-generating device before removal of the aerosol-generating article from the heating compartment and from the aerosol-generating device.

Alternatively, in the second position, the heating compartment may be fully removed from the chamber of the aerosol-generating device. In this aspect, the heating compartment containing a used aerosol-generating article may be fully removed to ease removal of the article. Less residues of aerosol-forming substrate may be loosened, when the heating compartment is fully removed before the used aerosol-generating article is removed from the heating compartment.

The heating compartment may be configured for positioning an aerosol-forming substrate in contact with the heating element such that the heating element is configured for penetrating an internal portion of the aerosol-forming substrate, wherein the heating compartment is configured for positioning the internal portion of the aerosol-forming substrate in contact with the heating element, and wherein the aerosol-generating device is configured such that an aerosol-generating article containing the aerosol-forming substrate is partly contained within the aerosol-generating device such that a user may puff on the aerosol generating article.

At least one air inlet may be provided between the heating compartment and an inserted consumable. The air inlet may be provided as a groove in the heating compartment such that the consumable may be firmly held within the heating compartment while air may pass between the heating compartment and the consumable.

The aperture in the base end of the heating compartment for receiving the heating element may also be configured as a heating compartment air inlet such that air can be drawn through the aperture and guided past the heating element during use.

The device may comprise at least one air inlet, allowing air to pass between the heating compartment and the housing of the aerosol-generating device from the first open end of the heating compartment towards the base end of the heating compartment and through the aperture in the base end, when the heating compartment is in a first operating position. The air inlet according to this aspect aids in keeping the housing of the device cool enough for a user to be able to hold it with his or her fingers.

The first open end and the base end of the heating compartment may be connected by side surfaces. The heating compartment may comprise openings at the side surfaces of the compartment.

In this way, the heating compartment may be configured flexible such that side surfaces of the heating compartment may be compressed during insertion into the chamber of the device. The heating compartment may be firmly held within the chamber due to a compressing action during insertion into the chamber. The consumable may be pressed together by the flexible sides of the heating compartment which may compress the substrate in the consumable. This may optimize the aerosol generation during operation of the induction heater.

The side surfaces may comprise locking elements to facilitate a snap-fit when the heating compartment is inserted into the chamber of the housing. The housing may comprise recesses corresponding to the locking elements. The heating compartment may comprise male locking elements and in the chamber of the housing female locking elements may be arranged and vice versa.

The heating compartment may comprise a press button for releasing the snap-fit for enabling the removal of the heating compartment from the chamber of the housing. The press button may compress side surfaces of the heating compartment such that locking elements in the side surfaces of the heating compartment disengage from corresponding locking elements in the chamber of the housing.

The heating compartment may comprise, at a second base end, an aperture such as a slit or holes for inserting the heating element into the heating compartment.

The heating element may not be integrally connected with the heating compartment. The heating element may be inserted through the slit or holes into the heating compartment during insertion of the heating compartment into the chamber of the device. The heating element may be part of the aerosol-generating device such that the heating element is provided in the chamber, while only the heating compartment without the heating element may be configured removable from the chamber. The extraction of a consumable may be optimized by providing a heating compartment and a separate heating element. A used consumable may be removed by removing the heating compartment. Thereafter, the used consumable may be removed from the heating compartment. Thus, the heating compartment may act as an extractor for extracting a used consumable from the device.

The device may comprise a controller. The controller may comprise a microprocessor, which may be a programmable microprocessor. The controller may comprise further electronic components. The controller may be configured to regulate a supply of electric power to the induction heater. Electric power may be supplied to the induction heater continuously following activation of the device or may be supplied intermittently, such as on a puff-by-puff basis. The power may be supplied to the induction heater in the form of pulses of electrical current.

The device may comprise a power supply, typically a battery, within the housing. As an alternative, the power supply may be another form of charge storage device such as a capacitor. The power supply may require recharging and may have a capacity that allows for the storage of enough energy for one or more puffs; for example, the power supply may have sufficient capacity to allow for the continuous generation of aerosol for a period of around six minutes or for a period that is a multiple of six minutes. In another example, the power supply may have sufficient capacity to allow for a predetermined number of puffs or discrete activations of the induction heater.

The aerosol-forming substrate may comprise homogenised tobacco material. The aerosol-forming substrate may comprise an aerosol-former. The aerosol-forming substrate preferably comprises homogenised tobacco material, an aerosol-former and water. Providing homogenised tobacco material may improve aerosol generation, the nicotine content and the flavour profile of the aerosol generated during heating of the aerosol-generating article. Specifically, the process of making homogenised tobacco involves grinding tobacco leaf, which more effectively enables the release of nicotine and flavours upon heating.

The induction heater may be triggered by a puff detection system. Alternatively, the induction heater may be triggered by pressing an on-off button, held for the duration of the user's puff.

The puff detection system may be provided as a sensor, which may be configured as an airflow sensor and may measure the airflow rate. The airflow rate is a parameter characterizing the amount of air that is drawn through the airflow path of the aerosol-generating device per time by the user. The initiation of the puff may be detected by the airflow sensor when the airflow exceeds a predetermined threshold. Initiation is however, preferably commenced upon a user activating a button.

The sensor may also be configured as a pressure sensor to measure the pressure of the air inside the aerosol-generating device which is drawn through the airflow path of the device by the user during a puff.

An aerosol-generating device as described above and a consumable may be an electrically operated smoking system. Preferably, the aerosol-generating system is portable. The aerosol-generating system may have a size comparable to a conventional cigar or cigarette. The smoking system may have a total length between approximately 30 millimetres and approximately 150 millimetres. The smoking system may have an external diameter between approximately 5 millimetres and approximately 30 millimetres.

The invention further relates to an aerosol-generating system comprising an aerosol-generating device as described above and an aerosol-generating article comprising an aerosol-forming substrate and configured for use with the aerosol-generating device.

Figure 1:
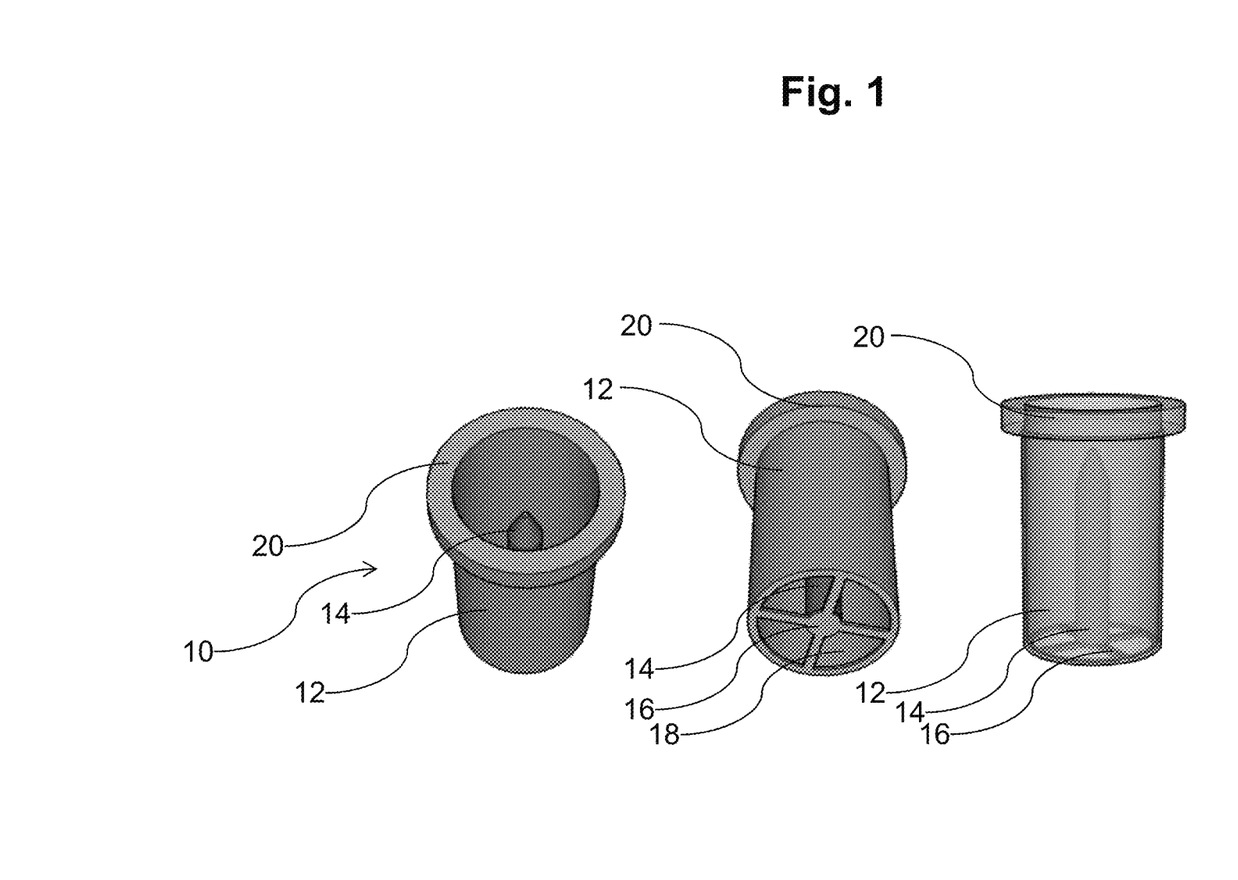
FIG. 1 shows a heating compartment comprising a heating element according to the invention from different perspectives.

FIG. 1 shows a heating compartment 10 from different perspectives. The heating compartment comprises a side surface 12. A heating element 14 is arranged within the side surface 12. The heating element 14 can be heated by a magnetic field generated by an AC current flowing through an induction coil. The induction coil surrounds the heating element 14. The magnetic field penetrates the heating element 14 and generated eddy currents in the heating element 14. These currents generate heat in the heating element 14.

The side surface 12 is arranged around the heating element 14. The heating element 14 is arranged along the longitudinal axis of the side surface 12. A support element 16 is provided at a base end of the heating compartment 10. The support member 16 connects the side surface 12 with the heating element 14. The support element 16 and the side surface 12 are made from a thermally insulating and electrically non-conductive material. The heating element 14 is made from an electrically conductive material. The support element 16 has a shape such that air can pass through apertures 18 in the support element 16.

At a first open end of the heating compartment 10, a protruding rim section 20 is provided for facilitating the insertion of the heating compartment 10 into a chamber of an aerosol-generating device. A consumable may be inserted into the heating compartment 10 at the first open end. The protruding rim section 20 has a diameter that is larger than the diameter of the side surface 12.

Figures 2, 2A, 2B, 2C:
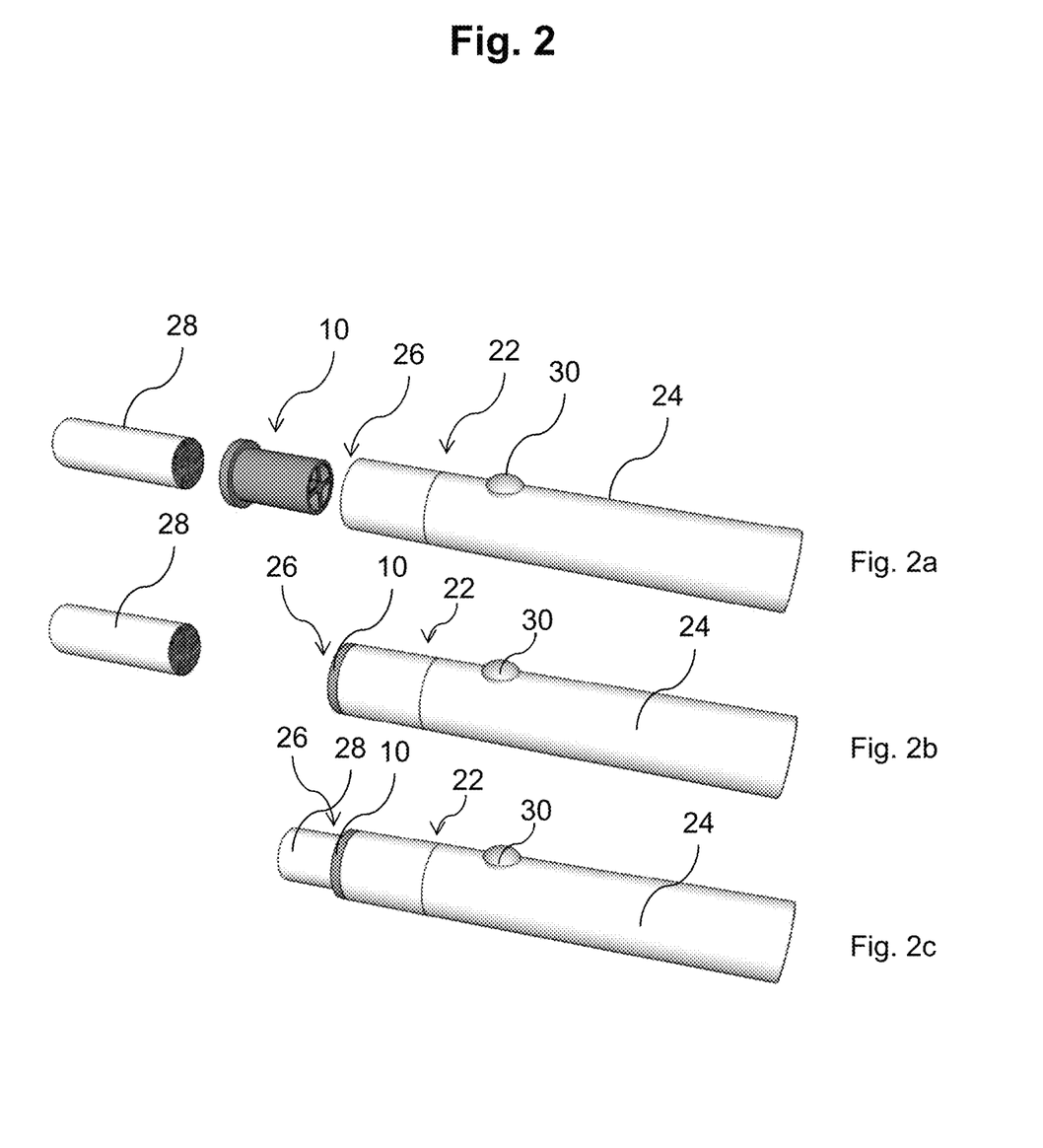
FIG. 2 shows the heating compartment depicted in FIG. 1 together with an aerosol-generating device.

FIG. 2 shows the heating compartment 10 depicted in FIG. 1 when inserted into an aerosol-generating device 22. The aerosol-generating device 22 has a modular construction comprising the heating compartment 10 and a housing 24. Within the housing 24, components of the aerosol-generating device 22 are provided such as a battery and a controller for controlling the flow of electrical energy from the battery to the induction heater. At a proximal end 26 of the housing 24, a chamber is provided in which the heating compartment 10 can be inserted. In walls within the housing 24 adjacent to the proximal end 26 of the housing 24, an induction coil is arranged. The induction coil together with the heating element 14 form the induction heater.

A aerosol-generating article in the form of a consumable 28 containing aerosol-forming substrate can be inserted into the heating compartment 10. FIG. 2a shows the consumable 28 before insertion into the heating compartment 10 and the heating compartment 10 before insertion into the chamber of the aerosol-generating device 22. In FIG. 2b, the heating compartment 10 has been inserted into the chamber of the aerosol-generating device 22. In FIG. 2c, the consumable 28 has been inserted into the heating compartment 10. The aerosol-generating device 22 comprises a button 30 for activating the induction heater.

Figures 3, 3A, 3B:
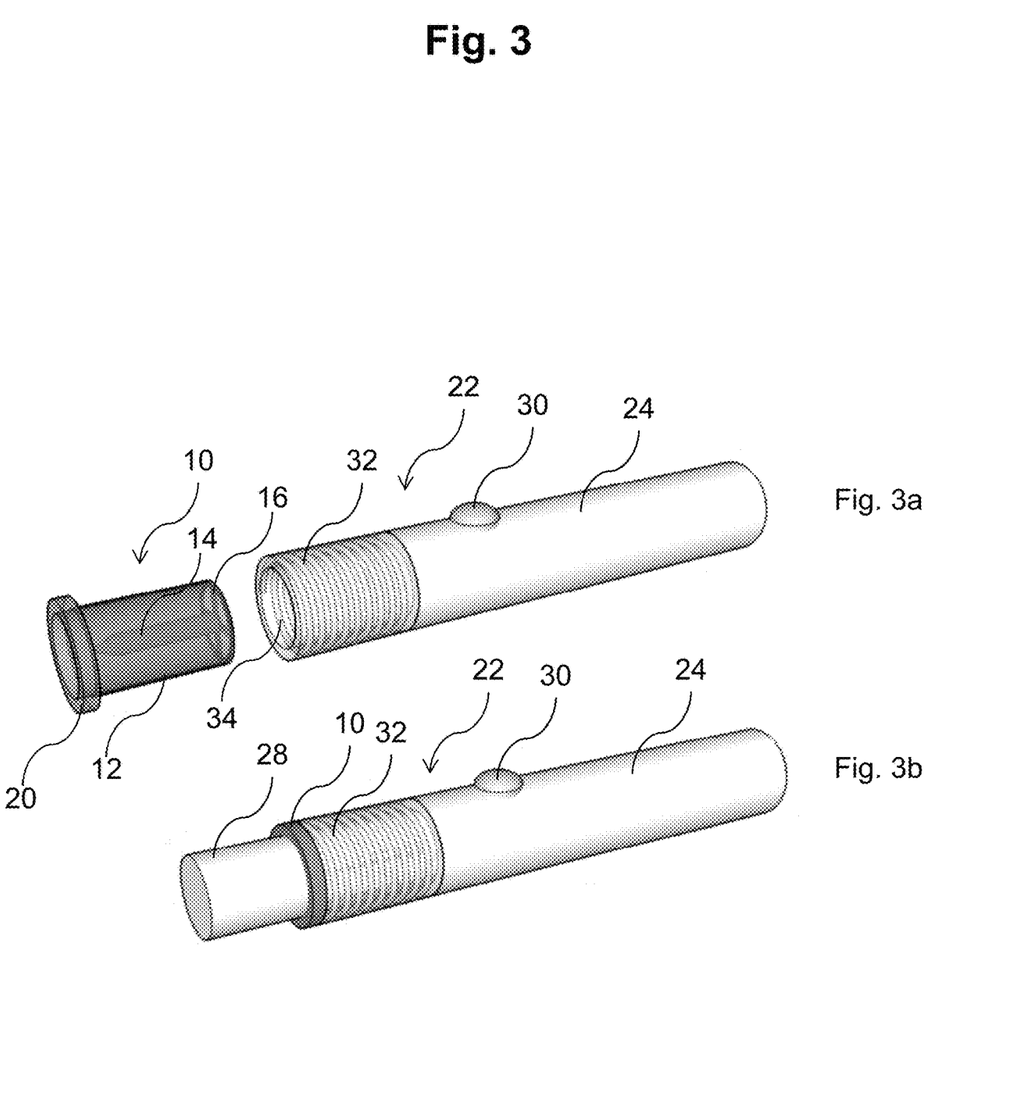
FIG. 3 shows the heating compartment inserted into a chamber of the aerosol-generating device.
Figure 4A:
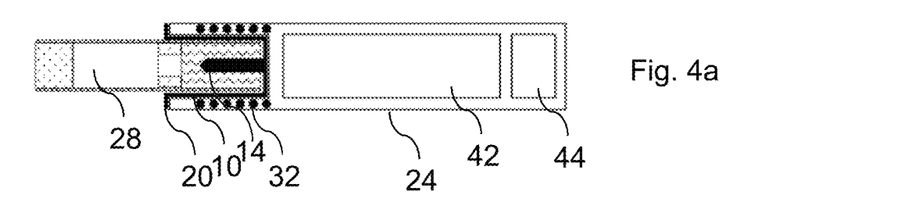
FIG. 4 shows an illustrative cross-sectional view of the aerosol-generating device with different air inlets.
Figure 4B:
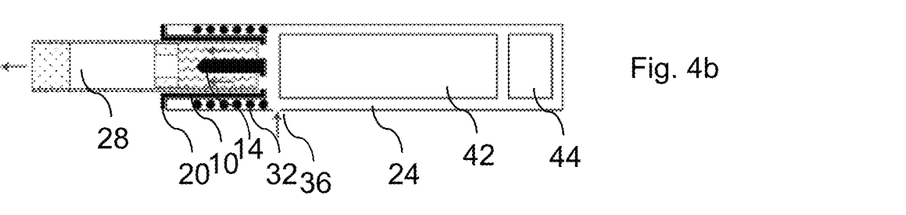
Figure 4C:
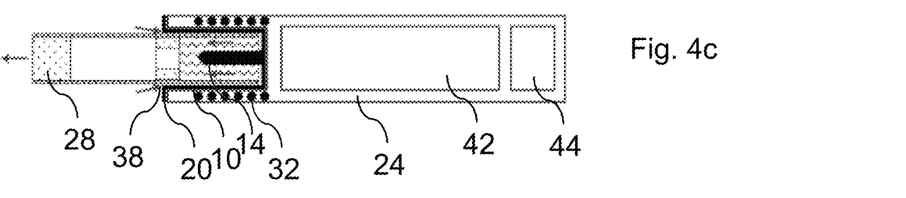
Figure 4D:
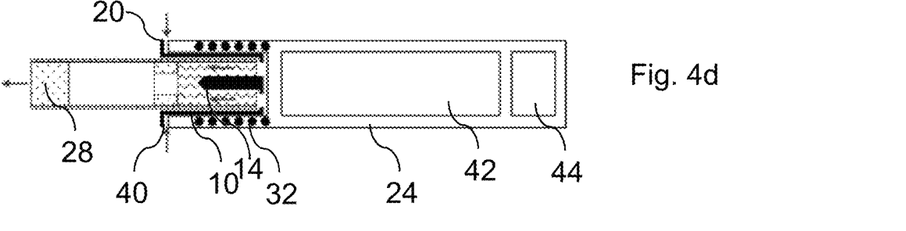

In FIG. 3, the walls of the aerosol-generating device 22 in which the induction coil 32 is arranged are depicted transparent and the chamber 34 can be seen in the aerosol-generating device 22. In FIG. 3a, the heating compartment 10 has not yet been inserted into the chamber of the aerosol-generating device 22. In FIG. 3b, the heating compartment 10 has been inserted into the chamber of the aerosol-generating device 22 such that the heating element 14 is surrounded by the induction coil 32.

In FIG. 4, the aerosol-generating device 22 is depicted with three different possible air inlets 36, 38, 40. In FIG. 4b, an air inlet 36 is provided at a side surface of the housing 24 of the aerosol-generating device 22. Ambient air can be drawn through the air inlet 36 into the aerosol-generating device 22 and guided through the consumable 28 for subsequent inhalation by a user. The direction of airflow is indicated by arrows. In FIG. 4c, an air inlet 38 is provided between the consumable 28 and the heating compartment 10. In this embodiment, the air inlet 38 is configured as a groove in the heating compartment 10. The consumable can be held firmly within the heating compartment 10, while air can be drawn into the device 22 between the heating compartment 10 and the consumable. In FIG. 4d, an air inlet 40 is provided between the heating compartment 10 and the housing 24 of the aerosol-generating device 22. Also in FIG. 4, the battery 42 and the controller 44 are depicted.

Figures 5, 5A, 5B:
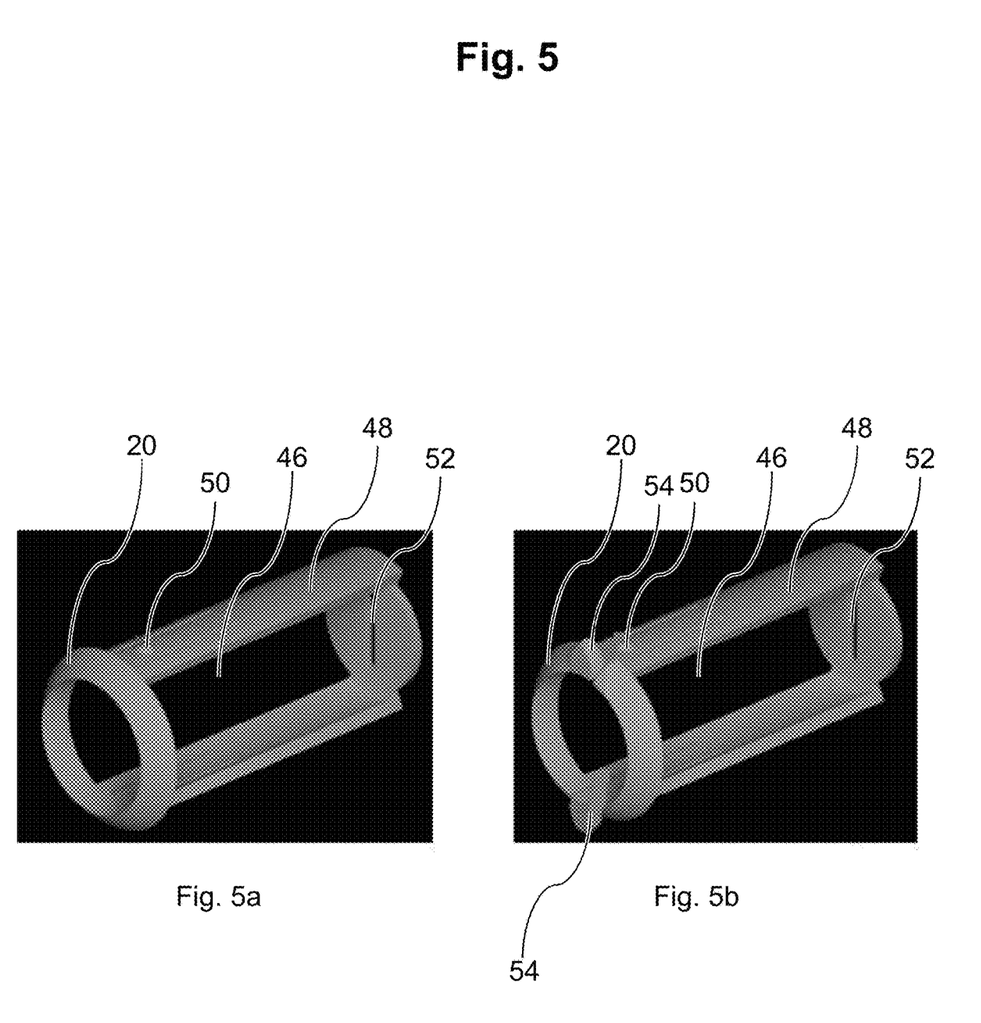
FIG. 5 shows different embodiments of the heating compartment with a separate heating element.

FIG. 5 shows the heating compartment 10 with openings 46 at the side surfaces 48. In this way, the side surfaces 48 may be compressed during insertion of the heating compartment 10 into the chamber 34 of the aerosol-generating device 22. The compressing of the side surfaces 48 may facilitate a firm fit of the heating compartment 10 within the chamber 34 of the aerosol-generating device 22. Also, a firm fit is thereby generated between the side surfaces 48 and a consumable 28. For further securing the heating compartment 10 within the chamber 34 of the aerosol-generating device 22, locking elements 50 may be provided at the side surfaces 48 with corresponding locking elements at the chamber 34 of the aerosol-generating device 22. FIG. 5 also shows an embodiment in which the heating element 14 is not connected with the heating compartment 10. Instead, a slit 52 is provided for enabling an insertion of a heating element 14 with a blade shape. Also, instead of the slit 52, holes may be provided for inserting pin-shaped heating elements 14.

The heating compartment 10 can be inserted into the chamber 34. When a consumable 28 is inserted into the heating compartment 10, the device is operable and in a first position. When the heating compartment 10 is retracted or removed from the chamber 34 and the consumable 28 removed from the heating compartment 10, he device is not operable and in a second position.

In FIG. 5b, an additional press-button 54 is depicted for releasing the locking elements 50 such that the heating compartment 10 can be removed from the chamber 34 of the aerosol-generating device 22.

The invention is not limited to the described embodiments. The skilled person understands that the features which are described in the context of the different embodiments can be combined with each other within the scope of the invention.

The invention claimed is:

1. An aerosol-generating device, comprising:
   a housing having a chamber,
   an induction coil disposed around at least a portion of the chamber;
   a heating compartment configured to receive an aerosol-generating article, the heating compartment being detachably insertable into the chamber of the housing, the heating compartment comprising a cavity configured to receive at least a portion of the aerosol-generating article; and
   a heating element arrangeable within the cavity of the heating compartment, wherein the heating element extends into the cavity in a longitudinal direction of the cavity, and wherein the heating element is configured to penetrate an aerosol-forming substrate comprised in the aerosol-generating article and received in the cavity,
   wherein the heating compartment further comprises a first open end configured to receive at least the portion of the aerosol-generating article, and a second, base end disposed opposite the first open end,
   wherein the first open end and the base end of the heating compartment are connected by side surfaces, the side surfaces comprising openings,
   wherein the side surfaces of the heating compartment comprise locking elements and the chamber of the housing comprises recesses corresponding to the locking elements of the heating compartment to facilitate a snap-fit when the heating compartment is inserted into the chamber of the housing, and
   wherein the heating compartment further comprises a press button configured to allow release of the snap-fit connection.

2. The aerosol-generating device according to claim 1, wherein the press button compresses the side surfaces of the heating compartment such that the locking elements in the side surfaces of the heating compartment disengage from the corresponding locking elements in the chamber of the housing.

3. The aerosol-generating device according to claim 1, wherein the heating element is not integrally connected with the heating compartment.

4. The aerosol-generating device according to claim 1, wherein the base end of the heating compartment comprises an aperture configured to receive the heating element.

5. The aerosol-generating device according to claim 4, wherein the aperture is a slit configured to enable an insertion of a heating element with a blade shape.

6. The aerosol-generating device according to claim 4, wherein the aperture is one or more holes configured for insertion of one or more pin-shaped heating elements.

7. The aerosol-generating device according to claim 1, wherein the side surfaces are compressed during insertion of the heating compartment into the chamber of the aerosol-generating device, and
   wherein compressing of the side surfaces facilitates a firm fit of the heating compartment within the chamber of the aerosol-generating device.

8. The aerosol-generating device according to claim 1, wherein the first open end of the heating compartment comprises a protruding rim with a width larger than an internal width of the chamber.

9. The aerosol-generating device according to claim 7, wherein the protruding rim has a same outer diameter as the housing of the aerosol-generating device and is configured to facilitate a smooth outer surface when the heating compartment is inserted into the chamber.

10. The aerosol-generating device according to claim 1, wherein the heating compartment is movably coupled to the chamber between a first position and a second position, the first position being an operating position defined by the heating element being in contact with the aerosol-forming substrate, and the second position being an extraction position defined by the aerosol-forming substrate being partly separated from the heating element.

11. The aerosol-generating device according to claim 10, wherein, in the second position, the heating compartment is partly removed from the chamber.

12. The aerosol-generating device according to claim 9, wherein the heating compartment is movably coupled to the chamber between a first position and a second position, the first position being an operating position defined by the heating element being in contact with the aerosol-forming substrate, and the second position being an extraction position defined by the aerosol-forming substrate being separated from the heating element.

13. The aerosol-generating device according to claim 12, wherein, in the second position, the heating compartment is fully removed from the chamber.

14. The aerosol-generating device according to claim 1, wherein the heating compartment forms part of an external housing of the aerosol generating device, when coupled to the aerosol generating device.

15. The aerosol-generating device according to claim 10, further comprising a guide pin configured to guide the heating compartment as the heating compartment is moved between the first and the second positions.

* * * * *